(12) United States Patent
Lahti et al.

(10) Patent No.: US 12,358,701 B2
(45) Date of Patent: **\*Jul. 15, 2025**

(54) TRAY COMPOSITE AND PACKAGE

(71) Applicant: AMCOR FLEXIBLES NORTH AMERICA, INC., Neenah, WI (US)

(72) Inventors: Hanna-Mari Lahti, Lempäälä (FI); Kaisa P. Putkisto, Tampere (FI)

(73) Assignee: Amcor Flexibles North America, Inc., Neenah, WI (US)

( \* ) Notice: Subject to any disclaimer, the term of this patent is extended or adjusted under 35 U.S.C. 154(b) by 839 days.

This patent is subject to a terminal disclaimer.

(21) Appl. No.: 17/295,816

(22) PCT Filed: Dec. 27, 2018

(86) PCT No.: PCT/US2018/067675
§ 371 (c)(1),
(2) Date: May 20, 2021

(87) PCT Pub. No.: WO2020/139343
PCT Pub. Date: Jul. 2, 2020

(65) Prior Publication Data
US 2022/0009683 A1    Jan. 13, 2022

(51) Int. Cl.
*B65D 65/40* (2006.01)
*B32B 1/00* (2024.01)
(Continued)

(52) U.S. Cl.
CPC ............... *B65D 65/40* (2013.01); *B32B 1/00* (2013.01); *B32B 7/06* (2013.01); *B32B 27/08* (2013.01); *B32B 27/10* (2013.01); *B32B 27/32* (2013.01); *B32B 27/34* (2013.01); *B32B 27/36* (2013.01); *B65D 1/34* (2013.01); *B65D 75/305* (2013.01); *B65D 81/343* (2013.01); *B32B 2307/718* (2013.01); *B32B 2307/7244* (2013.01);
(Continued)

(58) Field of Classification Search
CPC ......... B32B 27/08; B32B 27/32; B32B 27/12; B65D 65/40
USPC ........................................................ 206/557
See application file for complete search history.

(56) References Cited

U.S. PATENT DOCUMENTS

| | | | |
|---|---|---|---|
| 3,411,694 A | 11/1968 | Silver | |
| 4,455,184 A | 6/1984 | Thompson | |
| 4,543,280 A * | 9/1985 | Fujita | B32B 27/36 427/361 |
| 4,757,940 A | 7/1988 | Quick et al. | |
| 7,919,161 B2 | 4/2011 | Ebner et al. | |

(Continued)

FOREIGN PATENT DOCUMENTS

| | | |
|---|---|---|
| EP | 2965997 A1 | 1/2016 |
| WO | 2009138786 A3 | 11/2009 |
| WO | 2012122427 A3 | 12/2012 |
| WO | 2014108696 A1 | 7/2014 |

(Continued)

OTHER PUBLICATIONS

PCT International Search Report, International application No. PCT/US2018/067675, issued Mar. 26, 2019, 2 pages.

*Primary Examiner* — Anthony D Stashick
*Assistant Examiner* — Raven Collins

(57) ABSTRACT

A tray composite comprises a polymeric based liner including an exterior surface layer, an interior surface layer, and a fiber based component removably affixed to the interior surface layer of the polymeric based liner. A release agent is located between the polymeric based liner and the fiber based component. The polymeric based liner and the fiber based component are manually separable after they have been removably affixed together.

20 Claims, 6 Drawing Sheets

(51) Int. Cl.
  *B32B 7/06*     (2019.01)
  *B32B 27/08*    (2006.01)
  *B32B 27/10*    (2006.01)
  *B32B 27/32*    (2006.01)
  *B32B 27/34*    (2006.01)
  *B32B 27/36*    (2006.01)
  *B65D 1/34*     (2006.01)
  *B65D 75/30*    (2006.01)
  *B65D 81/34*    (2006.01)

(52) U.S. Cl.
  CPC .......................... *B32B 2307/7246* (2013.01); *B32B 2307/748* (2013.01); *B32B 2439/02* (2013.01); *B32B 2439/70* (2013.01)

(56) References Cited

U.S. PATENT DOCUMENTS

| | | |
|---|---|---|
| 8,172,106 B2 | 5/2012 | Clamp et al. |
| 10,000,314 B2 | 6/2018 | Slack |
| 2005/0258575 A1 | 11/2005 | Kruse et al. |
| 2006/0286217 A1* | 12/2006 | Gelotte .............. B65D 77/2024 426/106 |
| 2015/0136764 A1 | 5/2015 | Dropsy et al. |
| 2017/0203534 A1 | 7/2017 | Lahti et al. |

FOREIGN PATENT DOCUMENTS

| | | |
|---|---|---|
| WO | 2015009518 A1 | 1/2015 |
| WO | 2016033682 A1 | 3/2016 |
| WO | 2017158233 A1 | 9/2017 |

* cited by examiner

TRAY COMPOSITE AND PACKAGE

BACKGROUND

This application is related to packaging suitable to hold a product component at one time and then aid in separation of the packaging parts for more environmentally friendly disposal after use of the product. Specifically, the packaging can be designed for food storage and oven cooking without compromising its integrity during use and separation for disposability post use. Fiber based trays with polymeric based liners have been used for many applications. These applications include packaging for various items, including industrial or consumer goods products and food products. A fiber based component of the tray has advantages of low cost, low weight, recyclability, thermal insulation, tangible haptics and high stiffness. The polymer based liner is added to enhance the physical properties of the tray, including sealing properties, moisture resistance, gas barrier, grease and flavor resistance and durability.

Often, the fiber based component is coated with a thin layer of polyethylene to achieve the benefits of a polymeric liner. However, more functionality can be obtained by using a premade polymeric liner and adhering it to the fiber based component. Premade liners, primarily made of polymers, are used in some applications where the fiber based component and the polymeric liner might be separated for disposal. However, often manual separation can be difficult or results in too much of the fiber based component remaining adhered to the premade liner after separation of the two components.

Fiber based trays that are designed for ovenable applications have used liners made of high temperature resistant polymers. Liners made of high temperature resistant polymers can be difficult to adhere to the fiber based component and require an additional adhesive component between the fiber based component and the liner. Additionally, the high temperature resistant polymeric liners can be even more difficult to remove from the fiber based component once they are adhered because of the added adherence caused by the heat.

SUMMARY

There is a need for a polymeric based liner for a fiber based tray that 1) can be removably affixed to a fiber based component of the tray components, 2) can survive oven temperatures and conditions without separating prematurely from the fiber based component nor adhering too much, and 3) can be easily manually separated from the fiber based component, especially after being subject to oven temperatures, for disposal of the parts separately.

The present application describes a tray composite that includes a polymeric based liner. The liner includes an exterior surface layer and an interior surface layer. A fiber based component is removably affixed to the interior surface layer of the polymeric based liner. A release agent is located between the polymeric based liner and the fiber based component, and the polymeric based liner and the fiber based component are manually separable after they have been removably affixed together.

One embodiment of the tray composite may include the same polymeric based liner, and the fiber based component of formable paper is removably affixed to the interior surface layer of the polymeric based liner across at least 90% of a surface area where the fiber based component is adjacent to the interior surface layer. This embodiment can also include the release agent located at an interface between the polymeric based liner and the fiber based component, such that when the polymeric based liner and the fiber based component are manually separated at the interface, 3% or less of a weight of the fiber based component remains affixed to the interior surface layer, and the force to separate the polymeric based liner and the fiber based component is at least 30 N/m and no more than 450 N/m.

Another embodiment of the tray composite may include the same polymeric based liner, and a fiber based component is removably affixed to the interior surface layer of the polymeric based liner across at least 90% of a surface area where the fiber based component is adjacent to the interior surface layer. This embodiment can also include a release agent located between the polymeric based liner and the fiber based component, and the polymeric based liner and the fiber based component are manually separable after they have been removably affixed together, such that after exposure to 220° C. oven conditions for 45 minutes the polymeric based liner remains removably affixed to the fiber based component over at least 80% of the surface area that the polymeric based liner and the fiber based component were removably affixed prior to oven exposure.

Any of the embodiments of the tray composite may have at least one inner layer located between the exterior surface layer and the interior surface layer, and such inner layer may be a barrier layer.

Any of the embodiments of the tray composite may enable: a force to separate the polymeric based liner and the fiber based component to be at least 10 N/m and no more than 500 N/m; the polymeric based liner and the fiber based component to be manually separable such that when separated 3% or less of a weight of the fiber based component remains affixed to the interior surface layer; and/or, the fiber based component is removably affixed to the interior surface layer across at least 90% of a surface area where the fiber based component is adjacent to the interior surface layer.

Any of the embodiments of the tray composite may locate the release agent in one or more of the interior surface layer and the fiber based component, at an interface between the polymeric based liner and the fiber based component, or substantially at the interface. As such, the polymeric based liner and the fiber based component may be manually separable at the interface, and even separable at substantially only the interface, most desirably.

Any of the embodiments of the tray composite may have the release agent as part of a carrier substrate located between the polymeric based liner and the fiber based component. The carrier substrate may be separate from the polymeric based liner and the fiber based component and affixed to one or both of them. Still further, the carrier substrate may be patterned between the polymeric based liner and the fiber based component, and the pattern may cover 50% to 100% of a surface area where the fiber based component is adjacent to the interior surface layer.

Any of the embodiments of the tray composite may be ovenable. For example, this may include the polymeric based liner being at least partially crosslinked. Additionally, or alternately, this may include the polymeric based liner remaining removably affixed to the fiber based component to between 90% and 300% of the extent in N/m that the polymeric based liner and the fiber based component were removably affixed prior to oven exposure, with oven exposure defined as exposing the tray composite to 220° C. oven conditions for 45 minutes. Additionally, or alternately, this may include the polymeric based liner remaining removably affixed to the fiber based component over at least 80% of the surface area that the polymeric based liner and the fiber based component were removably affixed prior to oven exposure.

Embodiments of the package may have a tray composite of any of the previous embodiments, plus a lid and a food product. The food product is hermetically sealed between the lid and the exterior surface layer of the polymeric based liner.

Yet another embodiment of the invention is a method of using any of the tray composites, and their optional features, as previously described. The method includes: obtaining a polymeric based liner, the liner including an exterior surface layer and an interior surface layer; obtaining a fiber based component that is removably affixed to the interior surface layer of the polymeric based liner and has a release agent located at an interface between the polymeric based liner and the fiber based component; and manually separating the polymeric based liner and the fiber based component after they have been removably affixed together.

BRIEF DESCRIPTION OF THE DRAWINGS

The disclosure may be more completely understood in consideration of the following detailed description of various embodiments of the disclosure in connection with the accompanying drawings, in which.

Figure 1:
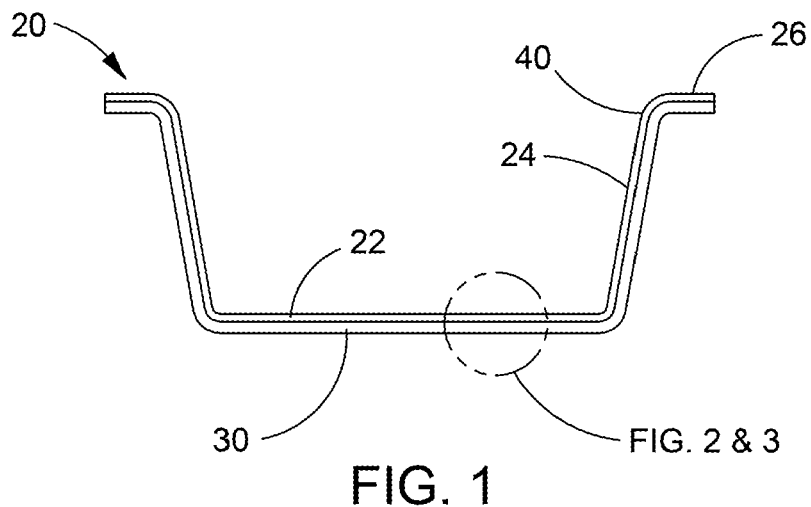
FIG. 1 is a cross-sectional view of an embodiment of a tray composite of the invention.

The drawings show some but not all features and embodiments. The elements depicted in the drawings are illustrative and not necessarily to scale, and the same (or similar) reference numbers denote the same (or similar) features throughout the drawings.

DETAILED DESCRIPTION

In accordance with the practice of at least one embodiment of the present invention, as seen in FIGS. 4-7, a package (10) includes a tray composite (20), a lid (12) and a food product (16). The product can be hermetically sealed within the package at least at seal (14). The product can be packaged and distributed for institutional use, catering or retail sale, through room temperature, refrigerated or frozen conditions. The package can be designed to be able to withstand heating in an oven for either cooking or reheating the product packaged therein. After use, involving heating or not, the tray composite parts can be manually separated for desired recycling and/or disposal.

Figure 2:
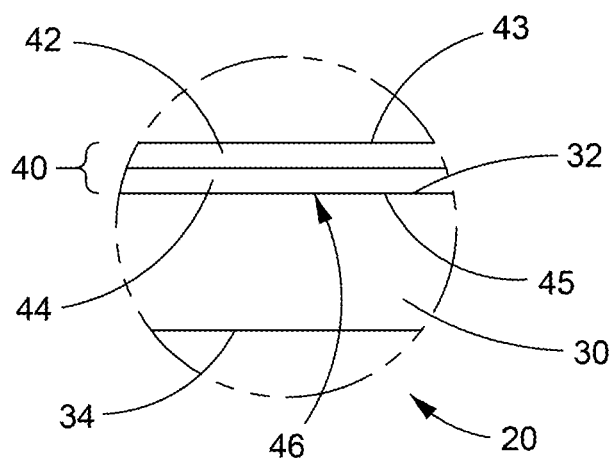
FIG. 2 is an exploded view of a portion of that seen in FIG. 1, as noted.

An embodiment of the tray composite (20) described herein is shown in FIGS. 1-2. The tray composite (20) includes a polymeric based liner (40), the liner including an exterior surface layer (42) and an interior surface layer (44). A fiber based component (30) is removably affixed to the interior surface layer (44) of the polymeric based liner (40). A release agent is located between the polymeric based liner (40) and the fiber based component (30). It is the inventors' unexpected discovery and innovative development to use a release agent as taught here that significantly enhances the polymeric based liner (40) and the fiber based component (30) being manually separable (peeled apart by hand) after they have been removably affixed together, better than possible without the release agent, but while also not negatively impacting the adhesion of the polymeric based liner (40) and the fiber based component (30) for use of the package and until disposal is desired.

That is, one challenge the present invention addresses with tray composite (40) is insuring enough adhesion between the polymeric based liner and the fiber based component so they act as one during use. Use includes both construction and assembly of the tray composite, e.g., converting (winding, unwinding, slitting, (thermo)forming, sealing, and all steps of packaging a product), locating the product or food product against the polymeric based liner, e.g., with or without a lid, through to removal of the product or food product from location against the polymeric based liner, and then eventual disposal of the tray composite. For example, this means the fiber based component (30) is removably affixed to the interior surface layer (44) across at least 90% of a surface area where the fiber based component (30) is adjacent to the interior surface layer (44). And, even more preferably, the fiber based component is removably affixed to the interior surface layer across at least 92%, 94%, 96%, 98% or substantially all of the surface area where the fiber based component (30) is adjacent to the interior surface layer (44).

Opposite the challenge to insure enough adhesion, is the challenge to enable manual separation of the polymeric based liner (40) and the fiber based component (30) once the product has been used or consumed and now the tray composite needs to be disposed of properly. Because these challenges oppose one another, enhancing one is at the detriment of the other, until discovery and development of the subject invention. Thus, there must be a balance between enough adhesion during use of the tray composite and not so much adhesion that the tray composite cannot be manually separated into its parts for disposal in a desirable way, e.g., an environmentally friendly way that enables recyclability per local regulations for doing so.

In this regard, in one embodiment of the invention the release agent is also located in one or more of the interior surface layer (44) and the fiber based component (30). For example, this can be achieved by adding the release agent to one of those layers during that layer's formation, most likely to the polymeric based liner (40), and in particular the interior surface layer (44), where some of the release agent slowly migrates out of the interior surface layer and locates itself against, on and inside of some of the adjacent interior surface (32) of the fiber based component (30). A desirable release agent, but not the only one, is known as a migratory additive. For a better understanding of the migratory additives that the inventors discovered work well as the present invention, see U.S. Pat. No. 10,011,086 of Bemis Company, Inc, granted Jul. 3, 2018. One particularly preferred additive is glyceryl monooleate, which can be included in polyethylene, for example, as 4 to 8 wt.-% of a 10%-active masterbatch of glyceryl monooleate in polyethylene, with the polyethylene and monooleate combination comprising some or all of the interior surface layer (44). Commercially available Ampacet POLYBATCH® AF 1088 of A. Schulman, Inc., Akron, OH, USA would contain such a preferred release agent. Without being limited to an amount of release agent to use, based on the Ampacet POLYBATCH® AF 1088 just discussed, it is believed that as much as 30 to 300 mg/m$^2$ of glyceryl monooleate may migrate to the interior surface (45) of the interior surface layer (44) over time. Some migration begins to happen upon formation of the polymeric based liner with the release agent, and then it continues. The migration rate (and thus amount to migrate over time) is particularly increased by subjecting the polymeric based liner to heat. It is this migration that locates the release agent between the polymeric based liner (40) and the fiber based component (30).

In another embodiment, the release agent is located at an interface (46) between the polymeric based liner and the fiber based component, such that the release agent is on and between the interior surface (45) of the interior surface layer and the interior surface (32) of the fiber based component. Even more preferred, the polymeric based liner and the fiber based component are manually separable at the interface to help in manually separating and doing so more cleanly so few, if any, fibers are torn from the interior surface (32) of the fiber based component and remain affixed to the interior surface (45) of the interior surface layer. Still more preferred, the polymeric based liner and the fiber based component are manually separable at substantially only the interface, thus achieving near perfect to perfect separation without a material amount of fibers being affixed to the interior surface (45) after separation of the polymeric based liner from the fiber based component.

Further in regard to the proper balance between adhesion during use of the package and separability for disposal, another embodiment of the invention can be practiced so the polymeric based liner (40) and the fiber based component (30) are manually separable such that when separated 5%, 4%, 3% or less of a weight of the fiber based component remains affixed to the interior surface layer. Even more preferred, the polymeric based liner and the fiber based component can be manually separable such that when separated 2% or 1% or less of a weight of the fiber based component remains affixed to the interior surface layer. Similar to this, and still more preferred, when the fiber based component is manually separated from the interior surface layer, the present invention now enables the user to substantially maintain and substantially uncompromise the structural integrity of the interior surface layer. That is, the act of manually separating will, desirably, not materially damage the interior surface layer.

Still further concerning the proper balance between adhesion during use and separability for disposal, a force to separate the polymeric based liner (40) and the fiber based component (30) for disposal is at least 10 N/m and no more than 500 N/m. Yet more preferred, the force to separate the polymeric based liner and the fiber based component is at least 30 N/m, 50 N/m, 80 N/m or 100 N/m and no more than 300 N/m, 350 N/m, 400 N/m or 450 N/m. The separation of the liner (40) from the fiber based component (30) is measured using tensile testing equipment according to ASTM F904. In particular, all aspects of the F904 test procedure should be employed as stated in F904 to make the measurements needed to determine the force to separate the identified parts of the tray composite after the package is subject to its intended use, except as follows: Section 8.3 test five specimens from the tray composite in its longitudinal direction and test five specimens from the tray composite made in its width direction (i.e., perpendicular to the longitudinal) with each set of five being its own force measurement contemplated by the invention here (and in the event the composite tray is square then picking one length or width direction as the longitudinal direction and the width direction as perpendicular to that), Section 10.1.1 condition for 40 hours, Section 11.1 only use mechanical means to start separation of the fiber based component from the polymeric based liner, Section 11.3.1 is used and not 11.3.2 nor 11.3.3, Section 12.1 is used and not 12.2.

Figure 8:
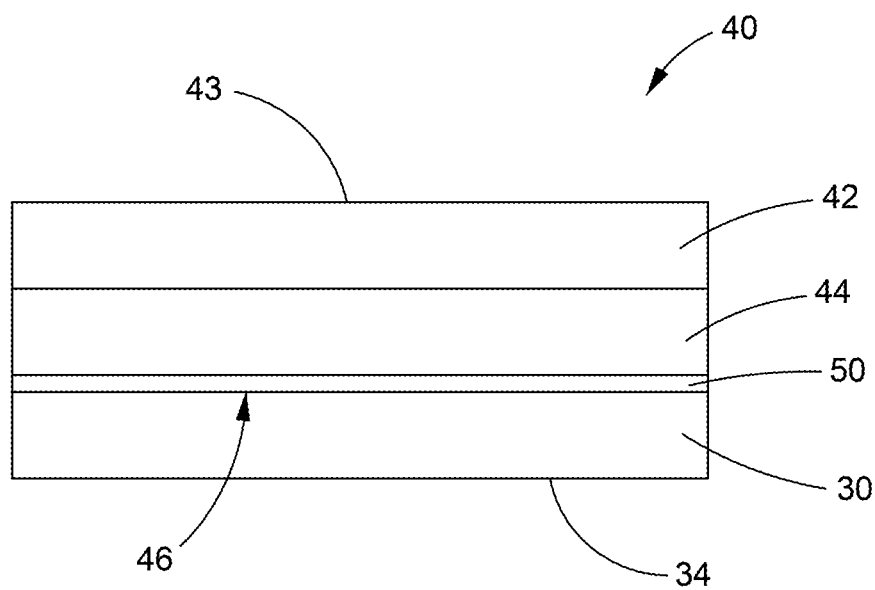
FIG. 8 is an exploded view of a portion of tray composite like that seen in FIGS. 2 and 3, but showing an alternate embodiment of the invention.

In another embodiment, the release agent is substantially located at the interface (46). For example, the release agent can be part of a carrier substrate (50) that is located between the polymeric based liner (40) and the fiber based component (30), as seen in FIG. 8. Preferably, the carrier substrate is distinct from the polymeric based liner and the fiber based component and affixed to one or both of them. This could be where the carrier is an ink, coating or adhesive, or other additive included on or between the fiber based component and the polymeric based liner. More preferably, the carrier substrate is patterned between the polymeric based liner and the fiber based component. This can be done to help achieve more adhesion in some areas versus others, e.g., at locations where a seal exists like (14) in FIGS. 4 to 6 to join a lid to the polymeric based liner (40) of package (10), while still balancing to not be too much adhesion that will prevent manual separation after use of the package. More preferred in this regard, the carrier substrate can be patterned to cover 50% to 100% of a surface area where the fiber based component is adjacent to the interior surface layer. For example, when the release agent is in or part of the carrier substrate as an ink, coating or adhesive, suitable materials include lower molecular weight soluble polymers, surfactants, micronized waxes and polymeric microparticles.

Figure 3:
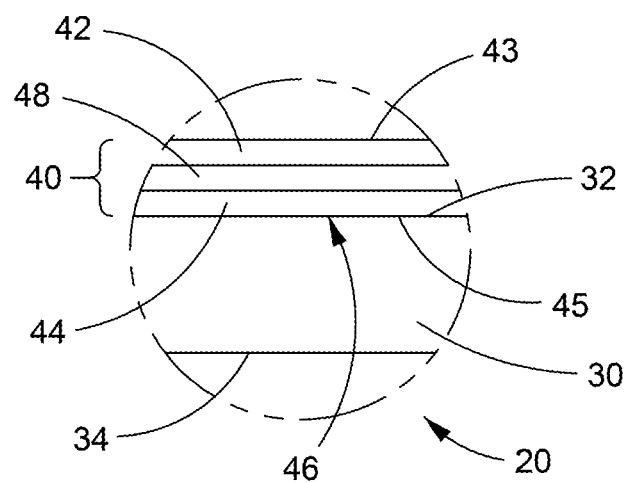
FIG. 3 is an exploded view of a portion of that seen in FIG. 1, as noted, but also showing an alternative embodiment of a tray composite.

In a different embodiment of the present invention, seen in FIG. 3, the polymeric based liner (40) further comprises at least one inner layer (48) located between the exterior surface layer (42) and the interior surface layer (44). The polymeric based liner (40) optionally contains any number of inner layers that may include polymers for functionality such as, but not limited to, interlayer adhesion (such as modified polyethylene tie layers), barrier (reducing transmission of oxygen, moisture or other chemical species), or structural enhancement (enhancing thermoformability, puncture strength, etc.). The polymeric based liner can have a thickness from about 25 µm to 500 µm, or from about 50 µm to 300 µm.

In one embodiment, the polymeric based liner (40) has an exterior surface layer (42) comprising polyester, a first inner layer comprising a first modified polyethylene, a second inner layer comprising a first polyamide, a third inner layer comprising a second modified polyethylene, a fourth inner layer comprising a second polyamide, a fifth inner layer comprising a third modified polyethylene, and an interior surface layer (44) comprising an ethylene vinyl acetate copolymer with a release agent additive. Alternately, the third modified polyethylene may also include a release agent additive. Still alternately, the third inner layer may comprise an ethylene vinyl alcohol copolymer.

In yet another embodiment, the tray composite is ovenable. For example, in part this can be achieved when the polymeric based liner is at least partially crosslinked within one or more of the polymer layers of the liner. The crosslinking can be achieved by any method, preferably irradiation from an electron beam generator, or as otherwise well known in the art. Crosslinking enhances the liner properties such that it can better survive the conditions of oven cooking. The fiber based component may (i) be removable affixed to the crosslinked polymeric based liner, (ii) have a coating on or in its material(s) or (iii) a combination of (i) and (ii), to enhance its ovenability. Typical coatings for ovenable fiber based materials include clay or polyester. Clay pigment coatings typically contain white mineral or organic pigments, a polymeric latex binder and auxiliaries. The inks used for printing may be ovenable. Ovenable cardboard products such as PrintKote® are available from WestRock Company.

Figure 9:
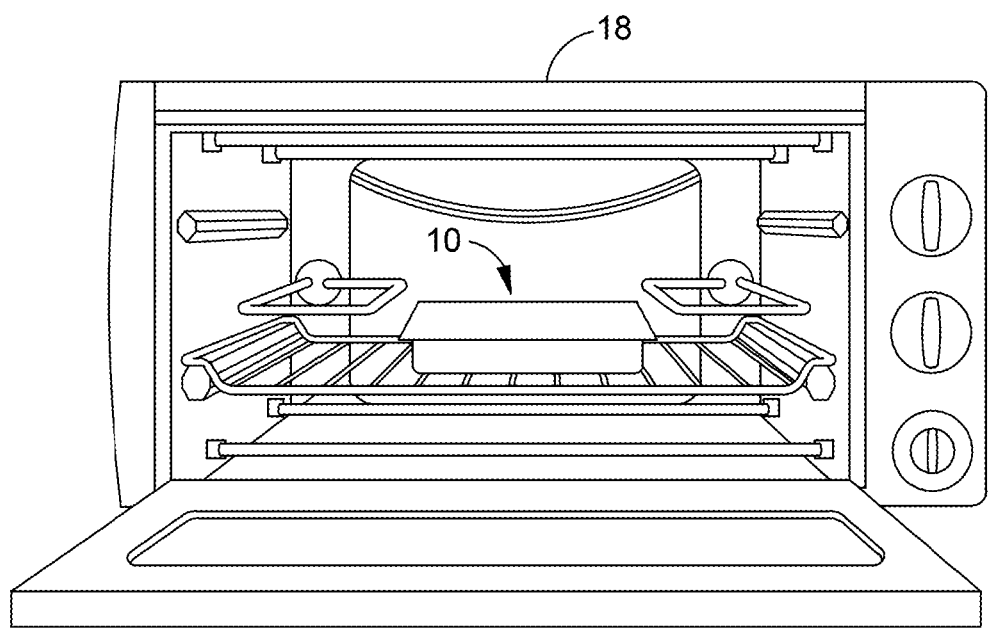
FIG. 9 is a view of an embodiment of a package in an oven.

FIG. 9 shows the package (10) inside an oven (18). As used in this application, a liner is heat resistant if it resists at least some separation from the fiber based component while experiencing heat and potential pressure increase (pressure internal to a fully or partially sealed package). This can be advantageous because, after exposure up to and including 125° C., 150° C., 175° C., 200° C. and 220° C. oven conditions for 15 up to 45 minutes, the polymeric based liner remains removably affixed to the fiber based component to between 90% and up to 100%, 150%, 200%, 250% and even 300% of the extent in N/m that the polymeric based liner and the fiber based component were removably affixed prior to oven exposure. For example, pre-ovening it may take 50 N/m to manually separate the fiber based component from the polymeric based liner, and after ovening it may take 150 N/m to manually separate the fiber based component from the polymeric based liner. This still obtains the separation taught by the invention as there will be little to no fibers remaining affixed to the separated liner and the separated liner integrity is not materially compromised. And, as compared to a material without a release agent, the release agent helps lower the extent in N/m it will take to separate the fiber based component from the polymeric based liner after ovening of the tray composite. Again, all this is achieving that very difficult balance of enough adhesion but not too much. Without the present invention, the adhesion between the fiber based component and the polymeric based liner is either too little before and/or after ovening and pre-mature separation occurs, or adhesion is too much after ovening and manual separation is difficult to impossible without substantial tearing of the fiber based component. Tensile testing equipment employed according to ASTM F904, and as instructed above, is used here also to determine the average force in N/m to separate the fiber based component from the polymeric based liner before, and then after, the package is subject to the oven temperatures for the stated time. Said another way, and also preferred, the polymeric based liner remains removably affixed to the fiber based component over at least 80%, 85%, 90%, 95%, to substantially all, most preferably, of the surface area that the polymeric based liner and the fiber based component were removably affixed prior to oven exposure.

The fiber based component of the tray can be, but is not limited to, paperboard, paper or other fiber based materials. The fiber based component can be a formable paper or a paperboard blank that can be folded into a tray type configuration. The fiber based component may have a part manufactured by a molded pulp process or a part produced directly from a natural raw material like wood or bamboo. The fiber based component may be part manufactured from polymer fibers. The fiber based component may be a single layer or multiple layers. A multilayer fiber based component can be achieved by laminating paper layers. Formable papers, such as FibreForm® (available from BillerudKorsnäs®) allow stretch and formability. Typically, formable papers are available in grades with basis weight of 80, 100, 150 or 200 g/m$^2$. The fiber based component should have stiffness and rigidity suitable for the application. Cardboard based trays preferably have a basis weight above 200 g/m$^2$. Rigidity of the formable paper based component can be adjusted with the basis weight and density of the paper layer or the paper layers and the accompanying polymer based layers. The required rigidity is largely dependent on the application and the size/design of the tray.

As used herein, the term "layer" refers to a thickness of a material or blend of materials that may be continuous or discontinuous. As used herein, the phrase "surface layer" as applied to film layers of the present disclosure refers to any film layer having less than two of its principal surfaces directly adhered to another layer of the film. In contrast, the phrase "inner layer," as applied to film layers, refers to any film layer having both its principal surfaces directly adhered to another layer of the film. The polymeric based liner can be produced using traditional film processing techniques such as blown film, cast film, or lamination. As used herein, the term "exterior surface" refers to a surface of the tray composite (such as the fiber based tray component or the polymeric based liner) that does not have contact with another tray component. Likewise, the "exterior surface layer" refers to the layer of the polymeric based liner that does not have contact with another tray component. The exterior surface layer of the polymeric based liner may have contact with other package components, such as the lid. As used herein, the term "interior surface" refers to a surface of the tray composite that is in contact with another tray component (such as the surfaces of the fiber based component and the polymeric based liner that are connected to each other). Likewise, the "interior surface layer" refers to the layer of the polymeric based liner that is in contact with another tray component, such as the fiber based component.

A preferred embodiment of the liner is produced by coextrusion. The exterior surface layer, the interior surface layer and any optional inner layers of the liner may be coextruded together (fully coextruded). Alternatively, any two or more adjacent layers could be coextruded together, and the remaining layers subsequently added in a different processing step, such as adhesive lamination, extrusion lamination, or coating.

Figure 4:
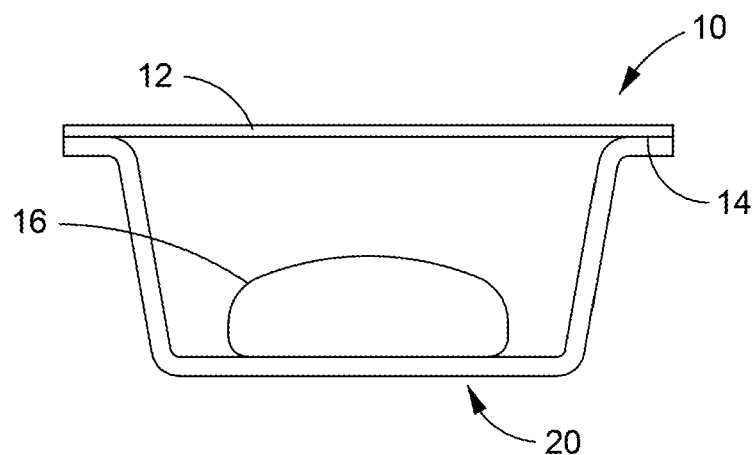
FIG. 4 is a cross-sectional view of the invention seen in FIG. 1, with a food product and a lid.
Figure 5:
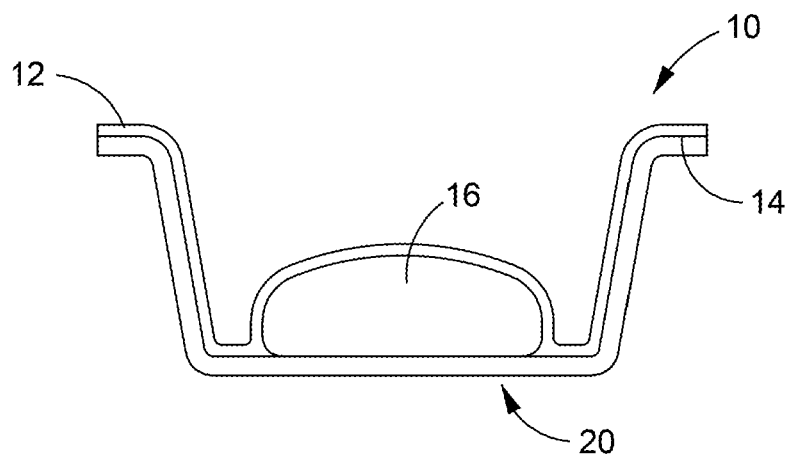
FIG. 5 is a cross-sectional view of the invention seen in FIG. 4, with the food product and an alternate lid embodiment.

The exterior surface layer (42) of the liner (40) can also be the layer that is connected to the lid (12) and any other components of the package (10). As shown in the embodiment of FIG. 4, the lid (12) is connected to the tray composite (20) using a hermetic seal (14) at the flange (26) of the tray. As shown in the embodiment of FIG. 5, the lid (12) is connected to the tray composite (20) using hermetic seal (14) along the flange (26) and portions of the sidewalls (24) and bottom (22) of the tray (20). The hermetic seal may be formed by any known method including heat sealing, ultrasonic sealing, RF welding, etc. The bond between the lid (12) and the tray composite (20) may be manually peelable for removal at the time of use to access the product. The material of the exterior surface of the liner can be configured for appropriate bonding to the lid and other package components such that a hermetic package can be formed for enclosing the food product (16) therein.

Prior to bonding to the fiber based component, the interior surface (45) of the polymeric based liner may be surface treated to increase the surface energy. This is advantageous to be better able to control the adhesion between the surface (45) of the polymeric based liner and interior surface (32) of fiber based component (30). As used herein, the phrase "surface treated" as applied to film layers refers to any technique which alters the surface energy (or surface tension) of a film layer and may include techniques such as, but is not limited to, corona, flame, and plasma treatment, ozone, ultra-high frequency electrical discharge, UV or laser bombardment, chemical priming, and the like. Surface treatment also helps enable the polymeric based liner to be connected to the fiber based component of the tray, under heated conditions, without the use of an additional adhesive material. That is, the polymeric based liner may be directly connected to the fiber based component. In other words, the polymeric based liner may be adjacent to the fiber based component. In one or more embodiments, the polymeric based liner and the fiber based component are connected and directly adjacent to each other. As used herein, "connected" or "directly connected" means that the components are attached to each other and would require a force to separate them. As used herein, "adjacent" or "directly adjacent" means that there is no intervening material between the components. As used herein, the terms "adhere," "adhered," "adhering," "adheres," "adherence," and "adhesion" as applied to film layers or other components of the present invention, are defined as affixing of the subject layer surface to another surface, with or without adhesive.

The polymeric based liner can be thermally laminated to a fiber based web, aka the fiber based component. The resulting composite tray material can be subsequently formed into a tray by thermoforming, press forming or other similar techniques, thereby forming the tray composite. Sufficient heat for lamination of the polymeric based liner to the fiber based component can be applied to the relatively thin liner, meaning that the process is not dependent on the thickness of the fiber based component. The type and thickness of the fiber based component generally does not affect the speed or efficiency of the thermal lamination process. Heat can be applied to the liner in a number of ways including, but not limited to convection heating by an industrial oven or direct contact heating. Direct contact heating may provide the most controlled heating. One method of direct contact heating can be done simultaneously with the lamination by using a heated nip roller system at the point where the polymeric based liner comes in contact with the fiber based component. The heated roller of the nipping system can be in contact with the exterior surface of the polymeric based liner and the backing rollers are located on the exterior surface of the fiber based component. Lamination can be controlled by the heated roller temperature, line speed (dwell time) and nip pressure. A textured or banded heated nip roller may allow for spot-bonding of the polymeric based liner to the fiber based component. This may allow for the provision of a peel tab at the edge of the tray component for ease of separation.

Optionally, the fiber based component of the tray can be pre-formed into the tray or receptacle configuration and the polymeric based liner subsequently heated and formed into the tray configuration and simultaneously bonded to the fiber based component. Again, the polymeric based liner can be heated by any methods. A particularly useful method is one that mimics the vacuum skin packaging (VSP) process used to apply lids to containers. In this case, there is no packaged item in the tray and the polymeric based liner material is heated and vacuum formed into the tray composite, simultaneously connecting to the fiber based component.

Using the heating and connecting techniques described herein, the polymeric based liner can be connected to the fiber based component without the assistance of an additional adhesive component. To enable the adhesive free connection process, the polymeric based liner must have an interior surface that will bond to the fiber based component at a level that will survive the rigors of the application for which the tray composite is being used.

Figure 10:
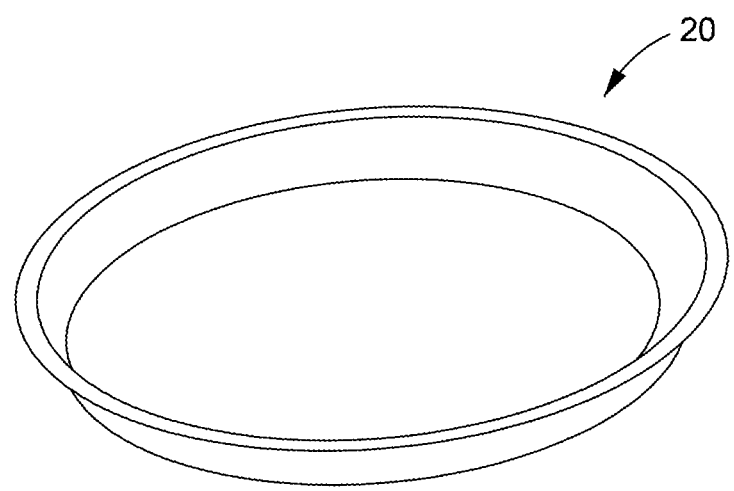
FIG. 10 is a view of another embodiment of a tray composite.
Figure 11:
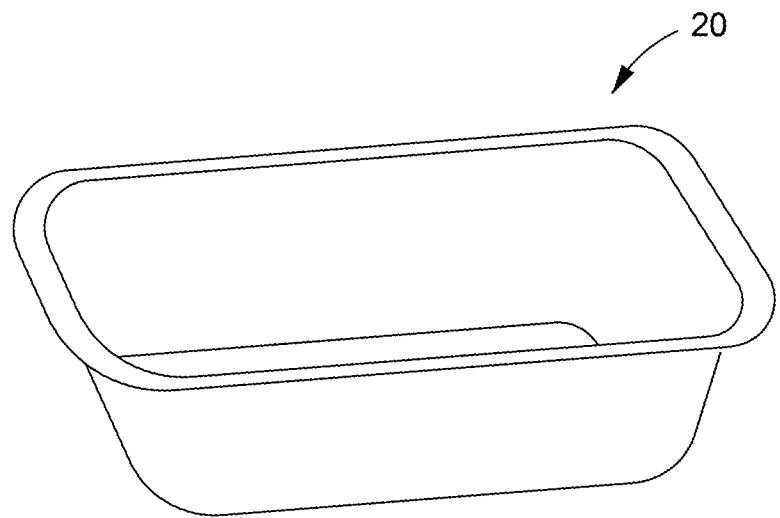
FIG. 11 is a view of yet another embodiment of a tray composite.
Figure 12:
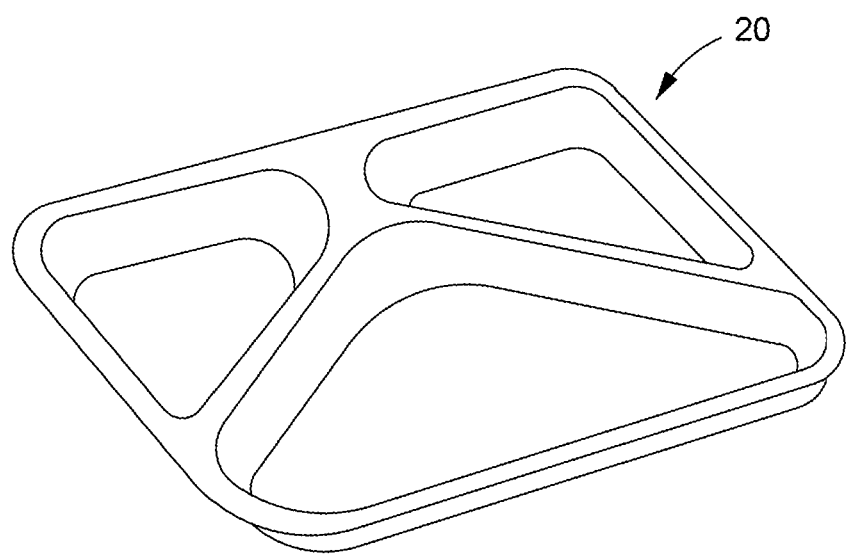
FIG. 12 is a view of still another embodiment of a tray composite.
Figure 13:
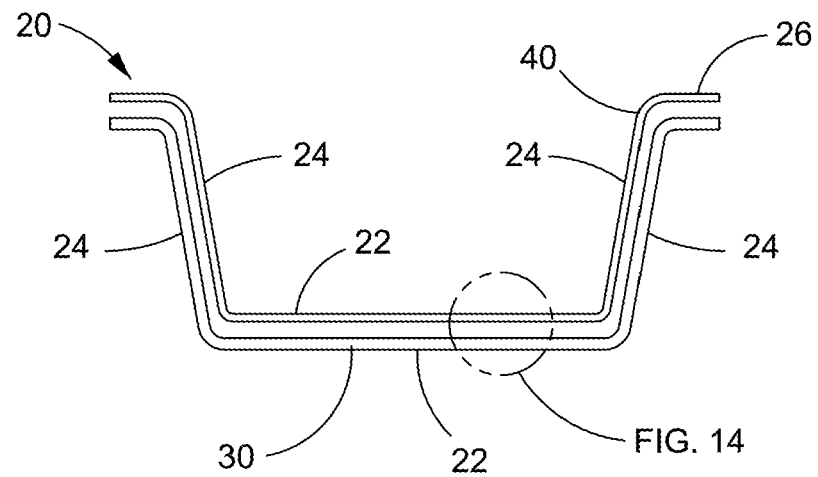
FIG. 13 is a cross-sectional view of the tray composite seen in FIG. 1, but now with the polymeric based liner separated from the fiber based component.
Figure 14:
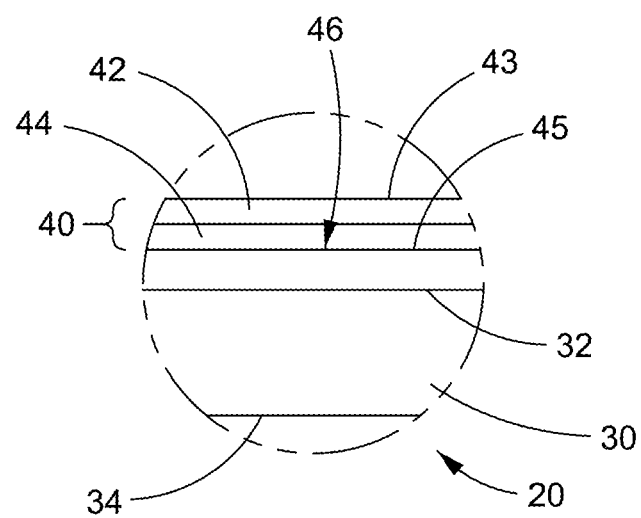
FIG. 14 is an enlarged view of a portion of that seen in FIG. 13, as noted, and the same embodiment as in FIG. 2.

The tray composite may be a receptacle, having a bottom, at least one sidewall and a flange as shown in FIGS. 10, 11 and 12. The tray may have more than one compartment as shown in FIG. 12. It has also been contemplated that the tray composite can be essentially a flat sheet with no formed areas, as in FIG. 7. In this case, the lid is sealed to the tray composite in the locations surrounding the packaged product.

Figure 6:
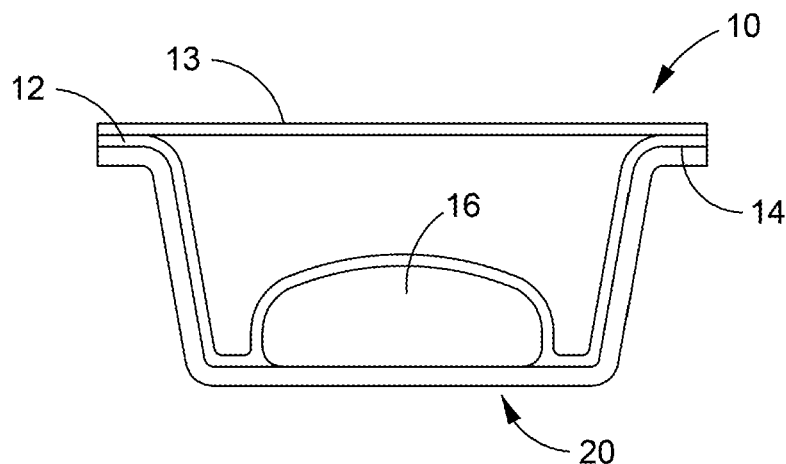
FIG. 6 is a cross-sectional view of the invention seen in FIG. 5, with the food product and an alternate lid embodiment.
Figure 7:
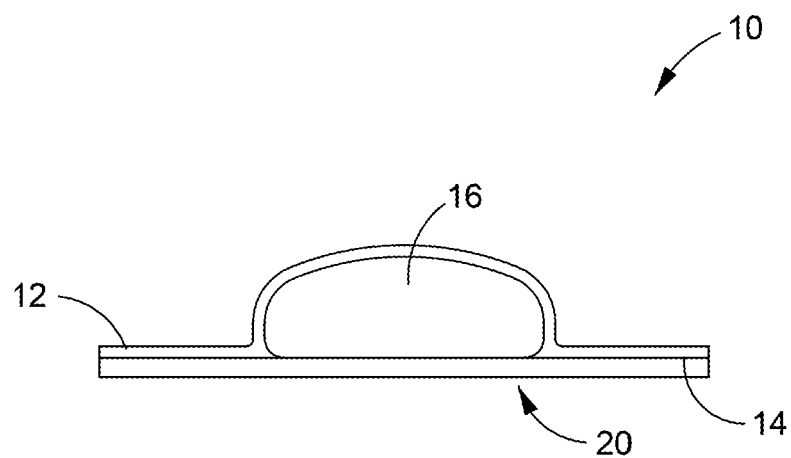
FIG. 7 is a cross-sectional view of an alternate embodiment of the invention seen in FIG. 1, with a food product and a lid.

The lid can be any type of lidding that can provide hermetic seals in combination with the sealant surface of the polymeric liner, adequate shelf life for the product prior to reheating and heat resistance up to 220° C. The seals described in this application may be formed by heat, impulse, ultrasonic, pressure or other seal-forming methods as known in the art. The lid may slightly or fully conform to the product within the package. The lid may be applied in a vacuum skin packaging (VSP) process or any other process known to the packaging industry. Multiple lids may be applied, such as a combination of a VSP lid (12) and a flat lid (13), as shown in FIG. 6. Bond strength may be higher at the intersection of joined parts beyond when the polymeric based liner is removably affixed to the fiber based component, e.g., where the lid (12) is joined to the tray composite as in FIGS. 4-7 and depending on whether ovenable or not.

The lid may be of a polymeric material, fiber based material, metal based material or combinations thereof. The lid may provide barrier, puncture resistance, or any other type of characteristic that would aid in protecting the product packaged therein. The lid may be opaque or transparent (or any gradient of transparency) and may be tinted or otherwise pigmented. The lid may have printed indicia on either side or within the layers thereof. It is further contemplated that the lid may be identical, or similar to, the tray component as described herein. This would result in a clamshell type packaging configuration.

The packages described herein can be filled with a wide variety of products. The products may be, but are not limited to, any type of consumer or industrial item, food or medical product, pharmaceutical, or heatable therapeutic device. The products can be items that consumers will want to heat, reheat or cook in an oven or warming device. As used herein, the term "oven" or "ovenable" refers to the process of heating, by any means, with the intent of raising the temperature of, or cooking, the contents within the package. Typical means for heating include conventional ovens using radiant heat, convection style ovens and microwave ovens. The oven conditions described herein refer to the environment around the package (external heating) or interior to the package (heating the packaged product via microwave, for example). Prior to oven heating, the lid component of the tray can be fully removed, partially removed (venting) or remain fully connected to the tray. Intense heating cycles may cause lids that are still connected to partially or fully disconnect from the tray—this can depend on the product within.

In yet another embodiment of the invention is disclosed a method of using the tray composite taught herein. The method includes obtaining a polymeric based liner, the liner including an exterior surface layer and an interior surface layer; obtaining a fiber based component that is removably affixed to the interior surface layer of the polymeric based liner and has a release agent located at an interface between the polymeric based liner and the fiber based component; and manually separating the polymeric based liner and the fiber based component after they have been removably affixed together. Additional features of the method are claimed below and will be understood as previously taught and described above and in the drawings.

Additional Discussion of the Embodiments

Embodiment 1: A tray composite that comprises: (a) a polymeric based liner comprising (i) an exterior surface layer and (ii) an interior surface layer; (b) a fiber based component removably affixed to the interior surface layer of the polymeric based liner; and (c) a release agent located between the polymeric based liner and the fiber based component, and the polymeric based liner and the fiber based component are manually separable after they have been removably affixed together.

Embodiment 2: The tray composite of embodiment 1, wherein the polymeric based liner further comprises at least one inner layer located between the exterior surface layer and the interior surface layer.

Embodiment 3: The tray composite of embodiment 2, wherein the at least one inner layer comprises a barrier layer.

Embodiment 4: The tray composite of any of the previous embodiments, wherein the fiber based component is a formable paper.

Embodiment 5: The tray composite of any of the previous embodiments, wherein a force to separate the polymeric based liner and the fiber based component is at least 10 N/m and no more than 500 N/m.

Embodiment 6: The tray composite of any of the previous embodiments, wherein the force to separate the polymeric based liner and the fiber based component is at least 30 N/m and no more than 450 N/m.

Embodiment 7: The tray composite of any of the preceding embodiments, wherein the release agent is also located in one or more of the interior surface layer and the fiber based component.

Embodiment 8: The tray composite of any of the preceding embodiments, wherein the release agent is located at an interface between the polymeric based liner and the fiber based component.

Embodiment 9: The tray composite of embodiment 8, wherein the polymeric based liner and the fiber based component are manually separable at the interface.

Embodiment 10: The tray composite of embodiment 9, wherein the polymeric based liner and the fiber based component are manually separable at substantially only the interface.

Embodiment 11: The tray composite of any of embodiments 8 to 10, wherein the release agent is substantially located at the interface.

Embodiment 12: The tray composite of any of the preceding embodiments, wherein the release agent is part of a carrier substrate that is located between the polymeric based liner and the fiber based component.

Embodiment 13: The tray composite of embodiment 12, wherein the carrier substrate is separate from the polymeric based liner and the fiber based component and affixed to one or both of them.

Embodiment 14: The tray composite of any of embodiments 12 to 13, wherein the carrier substrate is patterned between the polymeric based liner and the fiber based component.

Embodiment 15: The tray composite of embodiment 14, wherein the carrier substrate is patterned to cover 50% to 100% of a surface area where the fiber based component is adjacent to the interior surface layer.

Embodiment 16: The tray composite of any of the preceding embodiments, wherein the polymeric based liner and the fiber based component are manually separable such that when separated 3% or less of a weight of the fiber based component remains affixed to the interior surface layer.

Embodiment 17: The tray composite of any of the preceding embodiments, wherein the polymeric based liner and the fiber based component are manually separable such that when separated 1% or less of a weight of the fiber based component remains affixed to the interior surface layer.

Embodiment 18: The tray composite of any of the preceding embodiments, wherein the fiber based component is removably affixed to the interior surface layer across at least 90% of a surface area where the fiber based component is adjacent to the interior surface layer.

Embodiment 19: The tray composite of embodiment 18, wherein the fiber based component is removably affixed to the interior surface layer across substantially all of the surface area where the fiber based component is adjacent to the interior surface layer.

Embodiment 20: The tray composite of any of the previous embodiments, wherein the composite is ovenable.

Embodiment 21: The tray composite of any of the previous embodiments, wherein the polymeric based liner is at least partially crosslinked.

Embodiment 22: The tray composite of any of embodiments 20 to 21, wherein after exposure to 220° C. oven conditions for 45 minutes, the polymeric based liner remains removably affixed to the fiber based component to between 90% and 300% of the extent in N/m that the polymeric based liner and the fiber based component were removably affixed prior to oven exposure.

Embodiment 23: The tray composite of any of embodiments 20 to 22, wherein the polymeric based liner remains removably affixed to the fiber based component over at least 80% of the surface area that the polymeric based liner and the fiber based component were removably affixed prior to oven exposure.

Embodiment 24: A tray composite that comprises: (a) a polymeric based liner comprising (i) an exterior surface layer and (ii) an interior surface layer; (b) a fiber based component of formable paper removably affixed to the interior surface layer of the polymeric based liner across at least 90% of a surface area where the fiber based component is adjacent to the interior surface layer; and (c) a release agent located at an interface between the polymeric based liner and the fiber based component, and the polymeric based liner and the fiber based component are manually separable at the interface after they have been removably affixed together wherein (i) when separated 3% or less of a weight of the fiber based component remains affixed to the interior surface layer and (ii) the force to separate the polymeric based liner and the fiber based component is at least 30 N/m and no more than 450 N/m.

Embodiment 25: A tray composite that comprises: (a) a polymeric based liner that is at least partially crosslinked comprising (i) an exterior surface layer and (ii) an interior surface layer; (b) a fiber based component removably affixed to the interior surface layer of the polymeric based liner across at least 90% of a surface area where the fiber based component is adjacent to the interior surface layer; and (c) a release agent located between the polymeric based liner and the fiber based component, and the polymeric based liner and the fiber based component are manually separable after they have been removably affixed together, wherein after exposure to 220° C. oven conditions for 45 minutes the polymeric based liner remains removably affixed to the fiber based component over at least 80% of the surface area that the polymeric based liner and the fiber based component were removably affixed prior to oven exposure.

Embodiment 26: A package comprising: (a) a tray composite of any of the previous embodiments; (b) a lid; and (c) a food product; wherein the food product is hermetically sealed between the lid and the exterior surface layer of the polymeric based liner.

Embodiment 27: A method of using a tray composite that comprises: (a) obtaining a polymeric based liner comprising (i) an exterior surface layer and (ii) an interior surface layer; (b) obtaining a fiber based component that is removably affixed to the interior surface layer of the polymeric based liner and has a release agent located at an interface between the polymeric based liner and the fiber based component; and (c) manually separating the polymeric based liner and the fiber based component after they have been removably affixed together.

Embodiment 28: The method of embodiment 27, wherein a force to separate the polymeric based liner and the fiber based component is at least 30 N/m and no more than 450 N/m.

Embodiment 29: The method of any of embodiments 27 to 28, wherein the polymeric based liner and the fiber based component are manually separated at substantially only the interface.

Embodiment 30: The method of any of embodiments 27 to 29, wherein manually separating results in 3% or less of a weight of the fiber based component remaining affixed to the interior surface layer.

Embodiment 31: The method of any of embodiments 27 to 30, further comprising substantially maintaining and substantially uncompromising the structural integrity of the interior surface layer when the fiber based component is manually separated from the interior surface layer.

Embodiment 32: The method of any of embodiments 27 to 31, further comprising exposing the tray composite to 220° C. oven conditions for 45 minutes and the polymeric based liner remaining removably affixed to the fiber based component to between 90% and 300% of the extent in N/m that the polymeric based liner and the fiber based component were removably affixed prior to oven exposure.

Embodiment 33: The method of embodiment 32, further comprising maintaining the polymeric based liner removably affixed to the fiber based component over at least 80% of the surface area that the polymeric based liner and the fiber based component were removably affixed together prior to oven exposure.

Each and every document cited in this present application, including any cross referenced or related patent or application, is incorporated in this present application in its entirety by this reference, unless expressly excluded or otherwise limited. The citation of any document is not an admission that it is prior art with respect to any embodiment disclosed in this present application or that it alone, or in any combination with any other reference or references, teaches, suggests, or discloses any such embodiment. Further, to the extent that any meaning or definition of a term in this present application conflicts with any meaning or definition of the same term in a document incorporated by reference, the meaning or definition assigned to that term in this present application governs.

The present invention includes the description, examples, embodiments, and drawings disclosed; but it is not limited to such description, examples, embodiments, or drawings. As briefly described above, the reader should assume that features of one disclosed embodiment can also be applied to all other disclosed embodiments, unless expressly indicated to the contrary. Unless expressly indicated to the contrary, the numerical parameters set forth in the present application are approximations that can vary depending on the desired properties sought to be obtained by a person of ordinary skill in the art without undue experimentation using the teachings disclosed in the present application. Modifications and other embodiments will be apparent to a person of ordinary skill in the packaging arts, and all such modifications and other embodiments are intended and deemed to be within the scope of the present invention.

What is claimed is:

1. A tray composite that comprises:
   a) a polymeric based liner comprising:
      i) an exterior surface layer;
      ii) an interior surface layer; and
      iii) the exterior surface layer comprising first exterior surface of the tray composite;
   b) a fiber based component comprising second exterior surface of the tray composite and removably affixed to the interior surface layer of the polymeric based liner; and
   c) a release agent located between the polymeric based liner and the fiber based component, and the polymeric based liner and the fiber based component are manually separable after they have been removably affixed together.

2. The tray composite of claim 1, wherein the polymeric based liner further comprises at least one inner layer located between the exterior surface layer and the interior surface layer.

3. The tray composite of claim 2, wherein the at least one inner layer comprises a barrier layer.

4. The tray composite of claim 1, wherein the fiber based component is a formable paper.

5. The tray composite of claim 1, wherein a force to separate the polymeric based liner and the fiber based component is at least 10 N/m and no more than 500 N/m.

6. The tray composite of claim 5, wherein the force to separate the polymeric based liner and the fiber based component is at least 30 N/m and no more than 450 N/m.

7. The tray composite of claim 1 wherein the release agent is also located in one or more of the interior surface layer and the fiber based component.

8. The tray composite of claim 7, wherein the release agent is located at an interface between the polymeric based liner and the fiber based component.

9. The tray composite of claim 8, wherein the polymeric based liner and the fiber based component are manually separable at the interface.

10. The tray composite of claim 9, wherein the polymeric based liner and the fiber based component are manually separable at substantially only the interface.

11. The tray composite of claim 8, wherein the release agent is substantially located at the interface.

12. The tray composite of claim 1 wherein the release agent is part of a carrier substrate that is located between the polymeric based liner and the fiber based component.

13. The tray composite of claim 12, wherein the carrier substrate is separate from the polymeric based liner and the fiber based component and affixed to one or both of them.

14. The tray composite of claim 12, wherein the carrier substrate is patterned between the polymeric based liner and the fiber based component.

15. The tray composite of claim 14, wherein the carrier substrate is patterned to cover 50% to 100% of a surface area where the fiber based component is adjacent to the interior surface layer.

16. The tray composite of claim 1, wherein the polymeric based liner and the fiber based component are manually separable such that when separated 3% or less of a weight of the fiber based component remains affixed to the interior surface layer.

17. The tray composite of claim 1, wherein the fiber based component is removably affixed to the interior surface layer across at least 90% of a surface area where the fiber based component is adjacent to the interior surface layer.

18. The tray composite of claim 17, wherein the fiber based component is removably affixed to the interior surface layer across substantially all of the surface area where the fiber based component is adjacent to the interior surface layer.

19. The tray composite of claim 1, wherein the composite is ovenable.

20. The tray composite of claim 19, wherein the polymeric based liner is at least partially crosslinked.

* * * * *